United States Patent [19]

Fedan et al.

[11] 4,357,341
[45] Nov. 2, 1982

[54] SPECIFIC IRREVERSIBLE ANTAGONISM OF HISTAMINE RECEPTORS BY PHOTOAFFINITY ACTUATED COMPOUNDS

[75] Inventors: Jeffrey S. Fedan; John P. O'Donnell; G. Kurt Hogaboom, all of Morgantown, W. Va.

[73] Assignee: The United States of America as represented by the Department of Health and Human Services, Washington, D.C. ; a part interest

[21] Appl. No.: 266,462

[22] Filed: May 22, 1981

[51] Int. Cl.³ .......................................... A61K 31/415
[52] U.S. Cl. .................................. 424/273 R; 548/342
[58] Field of Search ...................... 548/342; 424/273 R

[56] References Cited

PUBLICATIONS

Hogaboom et al., *Science*, 208:1273–1276, Jun. 13, 1980.
Fedan et al., *European Journal of Pharmacology*, 69:41–53, 1981.
Chowdhry et al., *Ann. Rev. Biochem.*, 48:293–325, 1979.
Guillory et al., *Meth. Enzymology*, 46:259–288 (1977).
Bayley et al., *Meth. Enzymology*, 46:69–114 (1977).
Cooperman, *Ageing, Carcinogenicity and Radiation Biology*, Kendric (ed.), Plenum Press, NY, 1976, 315 ff.
Douglas, "Histamine and 5-Hydroxytryptamine (Serotonin) and Their Antagonists", *Goodman and Gilman's The Pharmacological Basis of Therapeutics*, 6th ed., Mc-Millan, 1980, pp. 609–619.

*Primary Examiner*—Richard A. Schwartz
*Attorney, Agent, or Firm*—John S. Roberts, Jr.

[57] ABSTRACT

Specific method of irreversible antagonism of histamine receptors, especially $H_1$ receptors, in, for example, isolated guinea pig vas deferens by 4(5)-[2-(4-azido-2-nitroanilino)ethyl]imidazole (AAH), which is a photoaffinity analog of histamine actuated unusually by light in the visible spectrum. Additionally, compounds of the present invention are represented by the formula

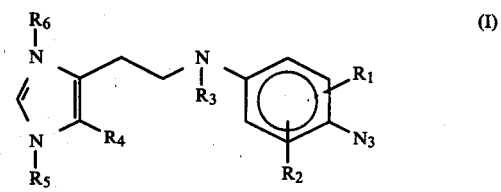

wherein $R_1$ and $R_2$ represent an electron withdrawing group of the formula, H, $-NO_2$, $-Cl$, $-F$, $-Br$, $-I$, $-SO_3H$. When two groups occur, it is not necessary that those groups be identical. In preferred compounds $R_1$ is $-NO_2$ and $R_2$ is H and $R_1$ is ortho to amine group.

$R_3$, $R_4$, $R_5$ and $R_6$ represent a proton or lower alkyl of straight and branched carbon chains. In preferred compounds $R_3$, $R_4$, $R_5$ and $R_6$ are protons or methyl groups with not more than two of the four positions substituted with an alkyl group. Preference is given for $R_4$ and $R_5$.

6 Claims, 6 Drawing Figures

SPECIFIC IRREVERSIBLE ANTAGONISM OF HISTAMINE RECEPTORS BY PHOTOAFFINITY ACTUATED COMPOUNDS

This application relates to a specific method of irreversible antagonism of histamine receptors, specially $H_1$ receptors, in, for example, isolated guinea pig vas deferens by 4(5)-[2-(4-azido-2-nitroanilino)ethyl]imidazole (AAH), which is a photoaffinity analog of histamine actuated unusually by light in the visible spectrum. Additionally, compounds of the present invention are represented by the formula wherein $R_1$ and $R_2$ represent an electron withdrawing group of the formula, H, $-NO_2$, $-CL$, $-F$, $-Br$, $-I$, $-SO_3H$. When two groups occur, it is not necessary that those groups be identical. In preferred compounds $R_1$ is $-NO_2$ and $R_2$ is H and $R_1$ is ortho to amine group.

$R_3$, $R_4$, $R_5$, and $R_6$ represent a proton or lower alkyl of straight and branched carbon chains. In preferred compounds $R_3$, $R_4$, $R_5$ and $R_6$ are protons or methyl groups with not more than two of the four positions substituted with an alkyl group. Preference is given for $R_4$ and $R_5$.

Photolysis of 4(5)-[2-(4-azido-2-nitroanilino)ethyl]imidazole (AAH) in organ chambers containing isolated guinea pig vas deferens resulted in an irreversible antagonism of histamine-induced contractions of the smooth muscle. A similar antagonism was found in the presence of non-photolyzed AAH and was reversible if not irradiated. After photolysis, AAH had no effect on tissue responses to KCl, norepinephrine and MgATP; responses to acetylcholine were only slightly reduced. Photolysis of AAH in the presence of diphenhydramine (DPH), an $H_1$-histamine receptor antagonist, protected the tissue from the effect of AAH. Histamine provided no protection, while cimetidine, an $H_2$-histamine receptor antagonist, was weakly protective. The results indicate that AAH is a specific and irreversible histamine photoaffinity antagonist. It satisfies the chemical and pharmacological criteria for such an antagonism. The antagonism appears to result from a covalent attachment of the compound to an $H_1$-histamine receptor-antagonist binding site.

The compounds of the present invention have present utility for blocking $H_1$ receptors of histamine in isolated tissue such as guinea pig ileum. The unusual utility lies in the fact that these compounds irreversibly antagonize histamine-induced contractions of the smooth muscle if irradiated with light in the visible spectrum, thus producing a specific and irreversible histamine photoaffinity antagonism.

Irreversible refers to the fact that the pharmacological antihistamine effect of aryl azido histamine persists after the compound is light activated and washed out of the bath. In other words, it still has a pharmacological effect so the fact that the behavior of the tissue does not return to the control indicates that the effect is irreversible.

The irradiation may be from the visible light and as such serves to make the compound an irreversible histamine photoaffinity antagonist. IR and UV also operate conventionally as a light source to produce irreversibility.

As to concentration, it has been found that a concentration of the active compound ranging from $3 \times 10^{-5}$ to $3 \times 10^{-6}M$ is sufficient to achieve the result intended for the guinea pig vas deferens.

It is also believed that the present compounds form covalent bonds with the $H_1$ receptors of histamine on photolysis. Thus, for example, AAH has the characteristic of a photoaffinity label in an intact tissue and it interacts with a histamine receptor leading to the formation of covalent bonds.

PRIOR ART STATEMENT

Hogaboom, O'Donnell, and Fedan, "Purinergic Receptors: Photoaffinity Analog of Adenosine Triphosphate Is a Specific Adenosine Triphosphate Antagonist," *Science*, 208:1273-1276, June 13, 1980.

Fedan, Hogaboom, O'Donnell et al, "Contribution by Purines to the Neurogenic Response of the Vas Deferens of the Guinea Pig," *European Journal of Pharmacology*, 69:41-53, 1981.

Chowdhry et al, "Photoaffinity Labeling of Biological Systems," *Ann. Rev. Biochem.*, 48:293-325, 1979.

Guillory and Jeng, "Arylazido Nucleotide Analogs in a Photoaffinity Approach to Receptor Site Labeling," *Meth. Enzymology*, 46:259-288 (1977).

Bayley et al, "Photoaffinity Labeling," *Meth. Enzymology*, 46:69-114 (1977).

Cooperman, "Photoaffinity Labeling of Proteins and More Complex Receptors," *Ageing, Carcinogenicity and Radiation Biology*, Kendric (ed.), Plenum Press, NY, 1976, 315 ff.

Douglas, "Histamine and 5-Hydroxytryptamine (Serotonin) and Their Antagonists," Goodman and Gilman's *The Pharmacological Basis of Therapeutics*, 6th ed., McMillan, 1980, pp. 609-619.

The compounds of the present invention and their activity appear different from the known prior art.

HISTAMINE

Histamine is 2-(4-imidazolyl)ethylamine. It is noted that some of the effects of histamine, such as bronchoconstriction and contraction of the gut or ileum are mediated by one type of histamine receptor, the $H_1$ receptors, which are reversibly blocked by pyrilamine and other such classical antihistamines, now more properly described as histamine $H_1$-receptor blocking drugs or simply $H_1$ blockers. The $H_2$ receptor antagonists, which are not of great interest in this application, have been little used except in the case of cimetidine for ulcer patients.

DESCRIPTION OF THE DRAWINGS

FIG. 4, left panel, shows the effect of DPH on histamine concentration-response curve. Open circles: control; closed circles: $10^{-6}$ M DPH. n=3. The right panel shows the effect of irradiation of AAH in the presence of DPH. Open circles: control; tissues were irradiated in the presence of $10^{-6}$ M DPH which was washed out before histamine was added. Closed circles: AAH-exposed; tissues were irradiated in the presence of $10^{-6}$ M DPH and $3\times10^{-5}$ M AAH, and both agents were washed out before histamine was added. n=8.

EXAMPLE 1

Synthesis of 4(5)-[2-(4-azido-2-nitroanilino)ethyl]imidazole hydrochloride

4-Fluoro-3-nitrophenylazide (1.8 g, 10.0 mmoles) was added to 11.0 ml of an aqueous solution of 4(5)-(2-aminoethyl)imidazole dihydrochloride (2.16 g, 12 mmoles) and Na₂CO₃ (324 mg, 30 mmoles). Ethanol-water (30 ml, 1:1) was added to enhance the homogeneity of the reaction. The mixture was stirred at 52° for 18 hours and the resulting dark red solution was concentrated under reduced pressure to about one-third of its volume and then diluted with 40 ml of 3 N HCl. The aqueous layer was extracted twice with 45 ml of ether. Subsequently the aqueous layer was adjusted to pH 7.0 and extracted with three 90 ml portions of methylene chloride. The combined methylene chloride layers following three washings, each with 50 ml of saturated NaCl, were dried (MgSO₄) and evaporated to dryness. The residue was taken up in ether and acidified with anhydrous HCl. The resulting precipitate was recrystalized from ethanol, yielding 2.1 g (58% yield) of product, mp 168-170 dec. NMR (MeOHd₃) δ 2.6-2.9 (m, 2H), 3.3-3.6 (m,2H), 6.8-7.5 (m,4H), 8.5 (2,H), mass spectrum m/e 273, 245, 199, 95, 82, 81. Anal.-Calc. for $C_{11}H_{12}N_7O_2Cl$; C,H,N. The structure of AAH is as follows:

EXAMPLE 2

Pharmacological Experiments

Adult, albino guinea pigs (250-350 g; Hilltop Lab Animals, Scottdale, PA) were killed by a blow to the head. Vasa deferentia were removed, desheathed and mounted in conventional apparatus for the measurement of isometric contractile responses. Each tissue preparation was bathed in a separate glass, water-jacketed organ chamber containing modified Krebs-Henseleit solution (37° C.) for one hour prior to the beginning of the experiment. The tissues were washed every 15 minutes. Resting tension was 200 mg. Agonist agents were added to the bath with stepwise increases in concentration. The agonists were added at 10 minute intervals and the tissues were exposed to each concentration for 2 minutes; the tissues were washed twice with agonist-free Krebs-Henseleit solution, at 5 minute intervals, between agonist additions.

The effects of AAH on the response of the smooth muscle of the guinea-pig vas deferens to several agonists were examined using the following protocols.

Figure 1:
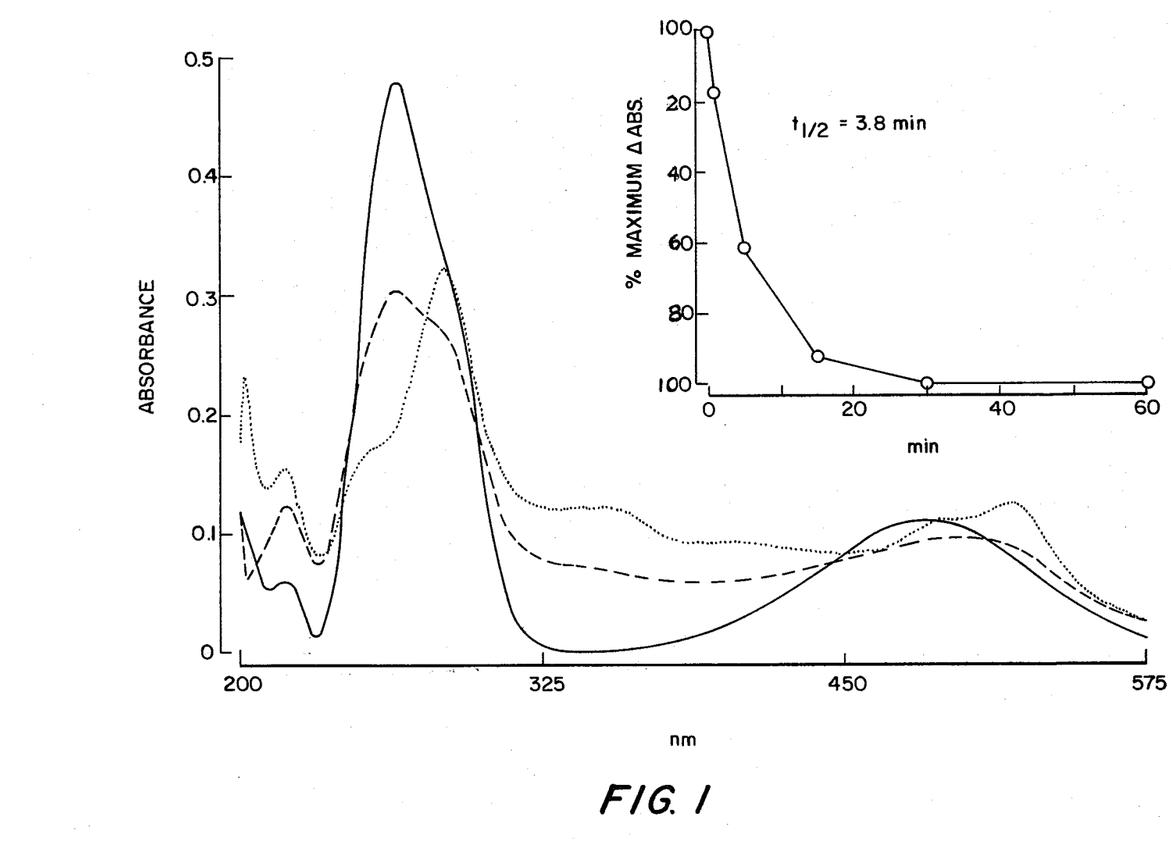
FIG. 1 is spectra of $3 \times 10^{-5}$ M AAH (dissolved in modified Krebs-Henseleit solution) sampled before (solid line) and 5 minutes (dashed line) and 60 minutes (dotted line) after the beginning of irradiation. The reference cuvette contained modified Krebs-Henseleit solution. The inset illustrates the time-course of decline in absorbance a 266 nm; data points were obtained from scans performed after the irradiation intervals shown. The $t_{\frac{1}{2}}$ for the first-order absorbance reduction was 3.8 minutes as calculated by linear regression analysis of log₁₀-transformed data.

Effect of AAH after photoactivation. While in the organ bath, one tissue of a pair was exposed to AAH for 5 minutes. The preparation was then irradiated with a tungsten-halogen projector lamp (DVY, 650 W, 3400° K., filament ca. 10 cm from the tissue) for 5 minutes. Bath temperature remained at 37° C. during irradiation. At the end of irradiation the tissues were washed twice with fresh Krebs-Kenseleit solution lacking AAH. Concentration-response determinations were begun 10 minutes after irradiation. Contralateral control tissues were irradiated in the absence of AAH and otherwise handled identically. FIG. 1 shows spectra of samples of AAH removed from the organ bath (no tissue present) before and at intervals after irradiation was begun. Also shown is the time-course of the decline of absorbance at 266 nm. The native spectrum, consisting of a pronounced peak at 266 nm, shoulder at 286 and broad peak at 480-485 nm, was changed by photolysis in a time-dependent manner to one with several smaller peaks and troughs. The absorbance reduction at 266 nm caused by photolysis showed first order kinetics with a $t_{\frac{1}{2}}$ of 3.8 min. The 5-minute photoaffinity labeling period used routinely produced ca. 62% of the maximum absorbance reduction.

Effect of AAH without photoactivation. Two types of experiments were performed with non-irradiated AAH. In the first type, the test tissue was exposed to AAH for 10 minutes but not irradiated during the latter five minutes; the AAH was washed out before agonist agents were added. That is, the same schedule as was used above was employed, but the preparations were not irradiated. In the second type of experiment with non-irradiated AAH, the compound was added to the bath 15 minutes before and remained present during the addition of agonists. The contralateral control tissues for these experiments received no treatment.

Effect of AAH after irradiation in the presence of histamine receptor ligands. Both vasa deferentia of a pair were exposed to histamine or diphenhydramine for 5 minutes. AAH was then added to the test tissue, leaving the control exposed only to ligand, and after a 5-minute incubation, both the test and control tissues were irradiated for 5 minutes. Both tissues were washed twice with fresh Krebs-Henseleit solution to remove all agents, and concentration-response determinations were performed 10 minutes after irradiation.

EXAMPLES 3-A

Effect of Photolyzed AAH on Histamine Concentration-Response Relationship

Figure 2:
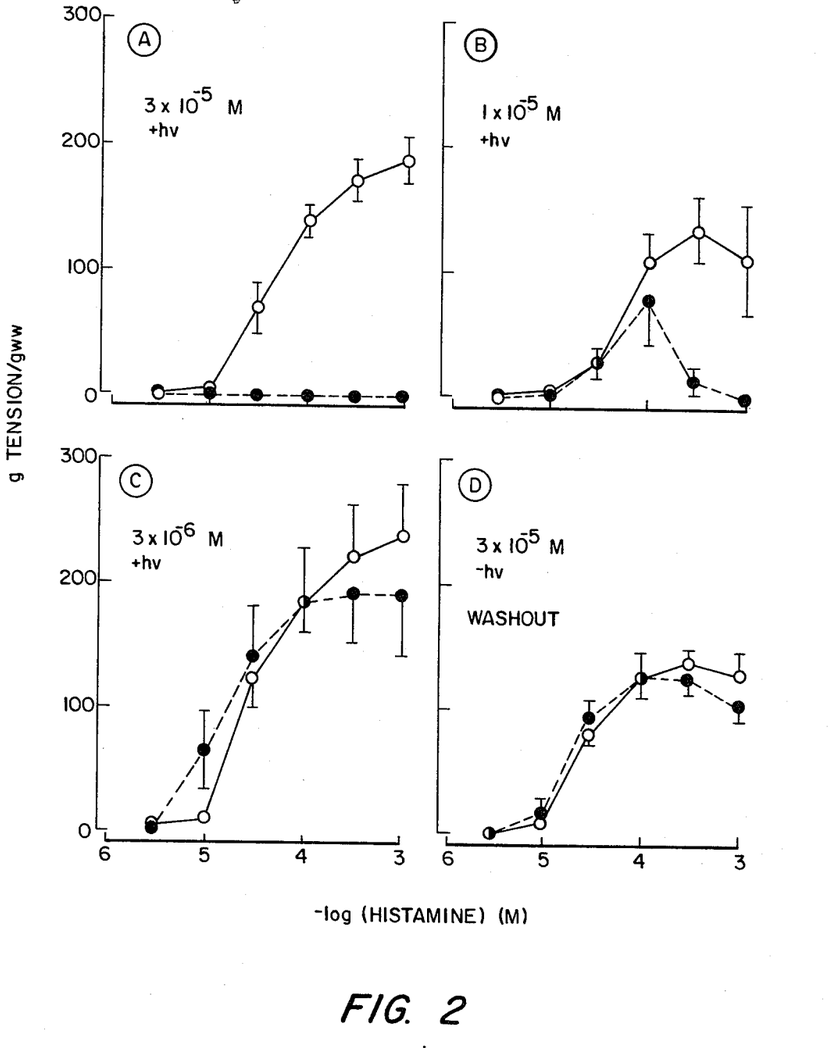
FIG. 2 shows histamine concentration-response curves following photolysis (5 minutes) and washout of $3\times10^{-5}$ M AAH (A; n=5), $10^{-5}$ M AAH (B; n=4) and $3\times10^{-6}$ M AAH (C; n=4). Open circles: irradiated control; closed circles: AAH-exposed and irradiated. In (D), the tissues (n=4) were exposed to $3\times10^{-5}$ M AAH as in (A), but the compound was not irradiated. AAH was removed by washing prior to the addition of histamine. Open circles: non-irradiated control; closed circles: AAH-exposed, not irradiated.

AAH in the concentrations used did not cause a contraction upon its addition to the organ bath. After its photolysis and washout, $3 \times 10^{-5}$ M AAH abolished the response of the tissues to histamine (FIG. 2A). This antagonism was not reversed by repeated washing of the tissues. A three-fold lesser concentration of AAH, $10^{-5}$ M, produced an intermediate and irreversible antagonism (FIG. 2B). The histamine concentration-response curve after photoactivation of $10^{-5}$ M AAH was "bell"-shaped, an effect not ordinarily produced by classical nonequilibrium competitive antagonists. In a concentration of $3 \times 10^{-6}$ M, AAH produced a small but significant decrease in the maximum response to histamine and a slight (1.89-fold) shift of the histamine concentration-response curve to the left of control (EC50 values were 4.16 (3.84–4.51)$\times 10^{-5}$ M and 2.20 (1.85–2.62)$\times 10^{-5}$ M for control and AAH-treated, respectively; $P<0.05$). Thus, the antagonism by AAH occurred over a narrow, 10-fold concentration range.

It was important to determine if the irreversible antagonism was dependent upon photolysis of the compound. FIG. 2D shows that $3 \times 10^{-5}$ M AAH had no residual effect on responses to histamine following a 10 minute incubation and subsequent washout when the compound was not photo-activated (EC50 values were 2.57(2.40–2.77)$\times 10^{-5}$ M and 2.10(1.82–2.44)$\times 10^{-5}$ M for control and AAH-treated, respectively).

Figure 3:
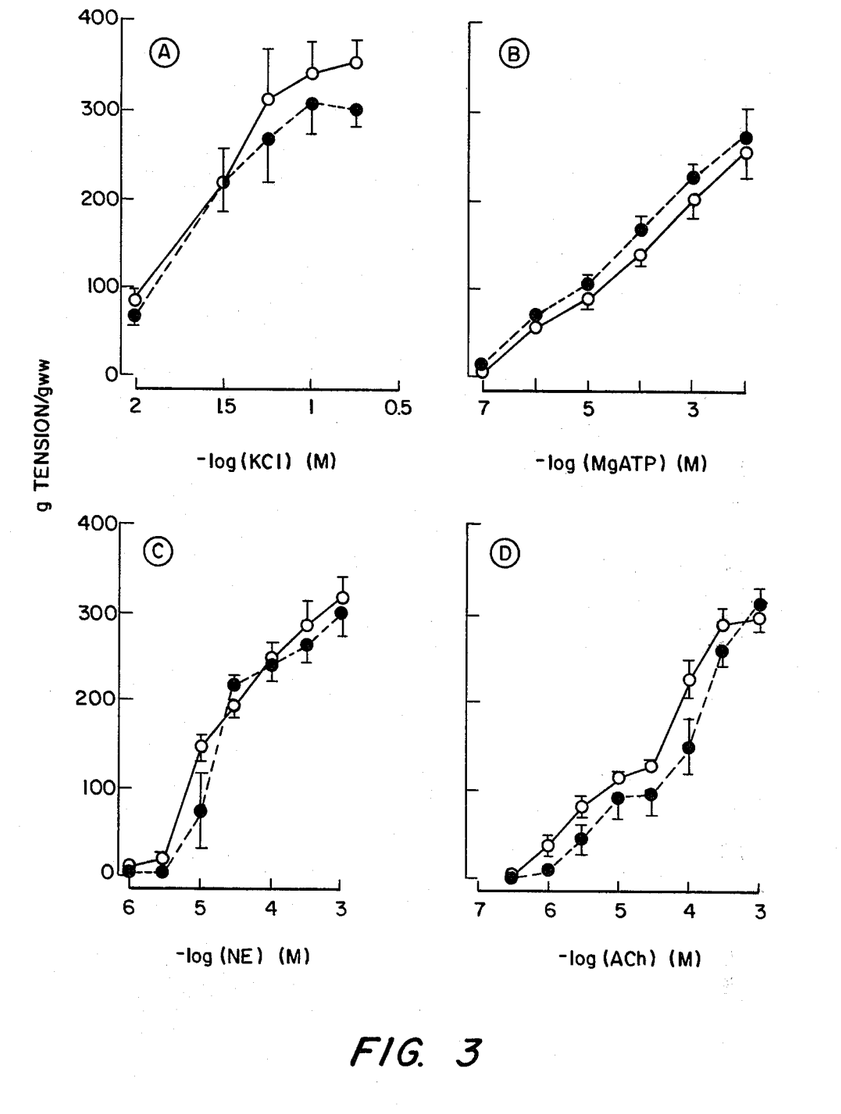
FIG. 3 shows concentration-response curves for (A) KCl, n=4, (B) MgATP, n=4, (C) norepinephrine (NE), n=3 and (D) acetylcholine (ACh), n=7 obtained following photolysis and washout of $3\times10^{-5}$ M AAH. Open circles: irradiated control; closed circles: AAH-exposed and irradiated.

Specificity of antagonism by photoactivated AAH. To test the possibility that the above antagonism by AAH may have resulted from a nonspecific toxic effect on the smooth muscle, the effect of photactivated AAH on the responses to other chemically unrelated excitatory agonists were examined. AAH ($3 \times 10^{-5}$ M), after photoactivation and washout, had no effect on the maximum responses or EC50's of KCl (control: 20.0(18.2–21.9) mM; AAH: 19.5(18.4–20.6) mM), MgATP control: 4.75(3.07–7.33)$\times 10^{-5}$ M; AAH: 2.35(1.51–3.64)$\times 10^{-5}$ M) and NE (control: 2.59(2.27–2.95)$\times 10^{-5}$ M; AAH: 2.26(1.37–3.77)$\times 10^{-5}$ M) (FIG. 3A–3C, respectively). This concentration of AAH did result in a small (3.07-fold) but significant shift of the ACh concentration-response curve to the right of control (control: 1.92(1.61–2.30)$\times 10^{-5}$ M; AAH: 5.90(3.56–9.80)$\times 10^{-5}$ M, $P<0.05$) (FIG. 3D); AAH had no effect on the maximum response to ACh. This small antagonism might be expected in view of the well-known antimuscarinic side-effects of antihistaminic drugs. These results indicate that the marked antagonism of histamine-induced responses by photoactivated AAH did not result from a nonspecific depression of the smooth muscle but rather from a selective interaction with the histamine receptor.

EXAMPLE 3-B

Effect of AAH Photolyzed in the Presence of Histamine Receptor Ligands

The irreversibility of the antagonism by photoactivated AAH (FIG. 2A) and the lack of an antagonistic effect of AAH when the compound was merely added to the bath and subsequently washed out (FIG. 2D) suggested that AAH became covalently bound to the receptor upon photolysis. When present during photoirradiation of AAH, other ligands which interact with the histamine receptor should, by their occupancy, prevent covalent attachment of AAH (Cooperman, 1976, vide supra) to the receptor and, hence, protect against the onset of the antagonism. Therefore, the ability of diphenhydramine (DPH), a classical $H_1$-receptor antagonist, and histamine to protect against the antagonism of photoactivated AAH was studied. DPH was first characterized for its ability to antagonize histamine.

Figure 4:
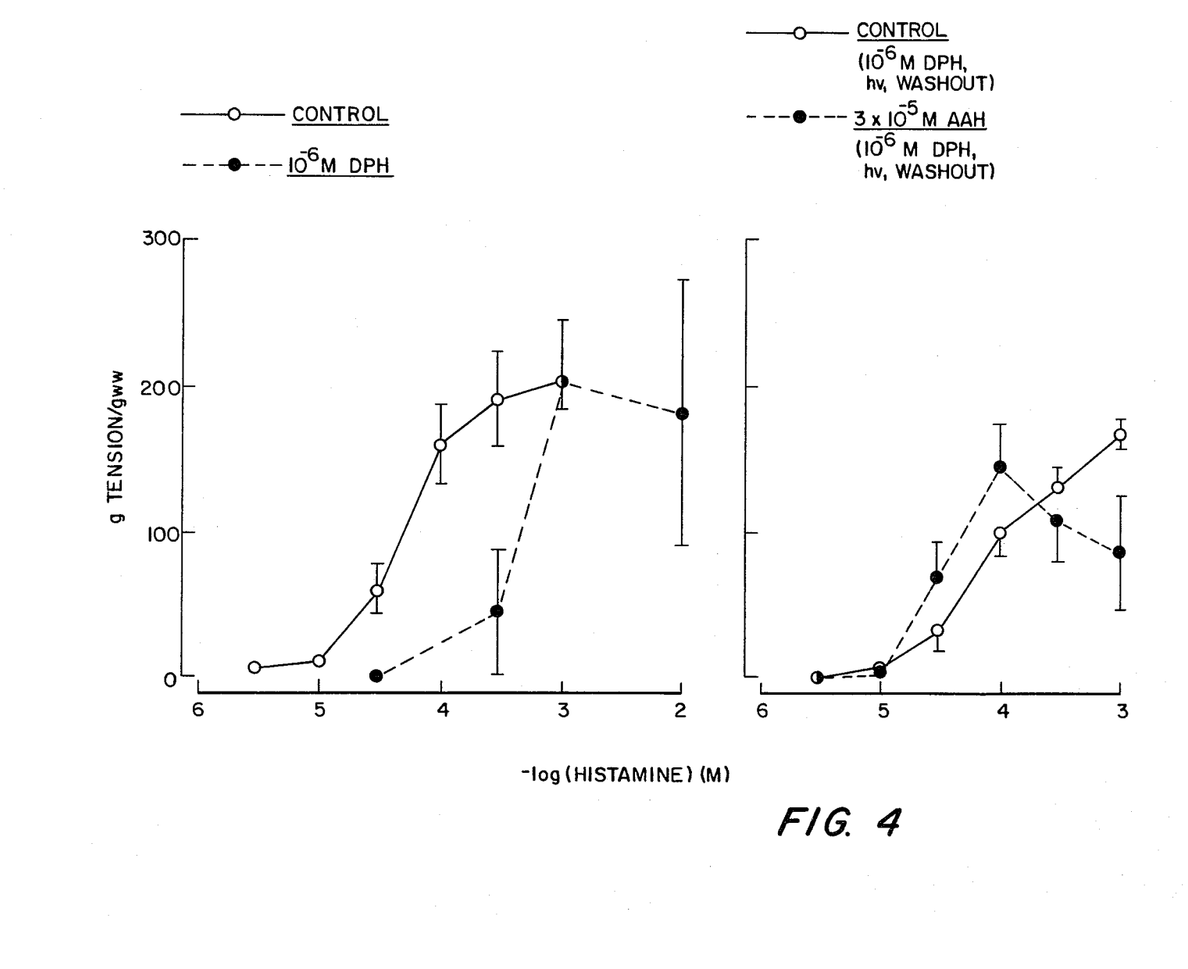
Figure 6:
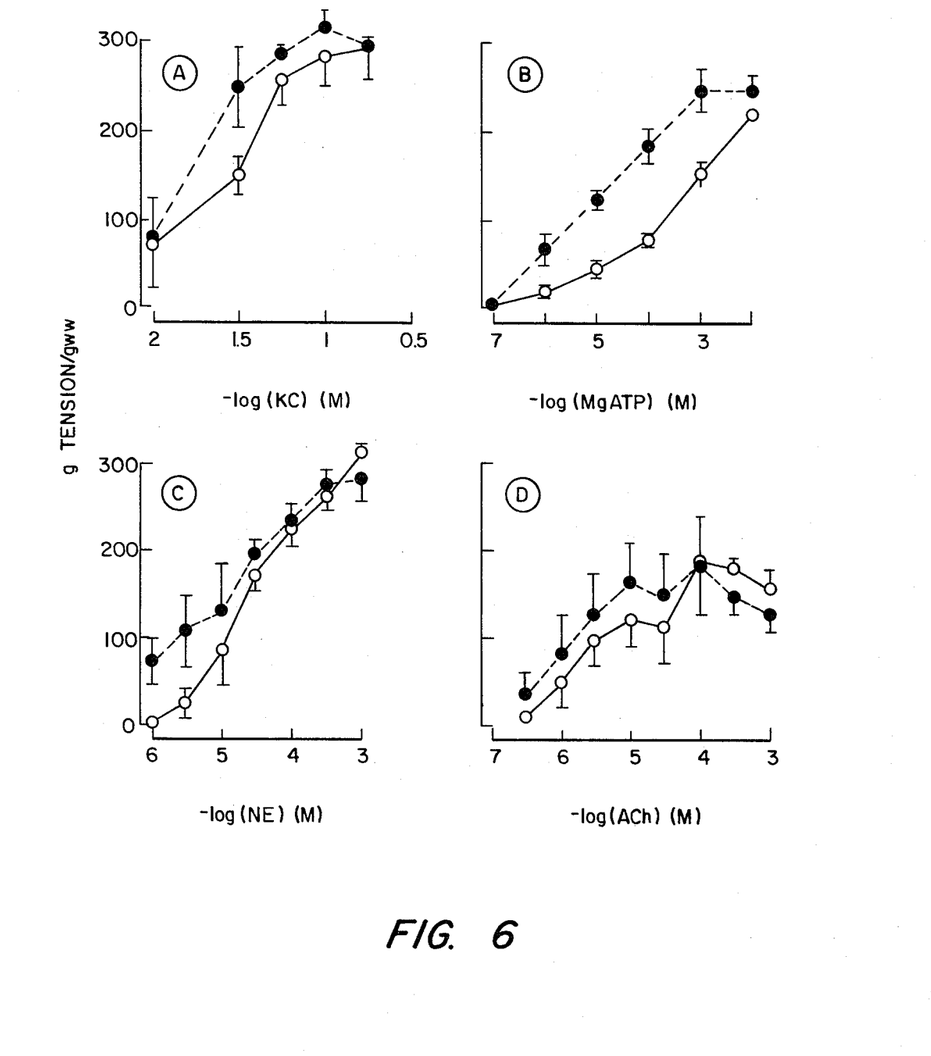
FIG. 6 shows concentration-response curves for (A) KCl, n=3, (B) MgATP, n=4, (C) norepinephrine (NE), n=3, and (D) acetylcholine (ACh), n=3, obtained in the continual presence of non-irradiated AAH ($3\times10^{-5}$ M). Open circles: non-irradiated controls; closed circles: AAH-exposed, continually present.

FIG. 6 (left panel) shows that $10^{-6}$ M DPH caused a 10-fold paralled shift of the histamine concentration-response curve to the right of control. This same concentration of DPH, when present in the organ bath during photolysis of $3 \times 10^{-5}$ M AAH (FIG. 4, right panel), protected against the development of AAH-induced antagonism (compare to FIG. 2A). In contrast, $3 \times 10^{-4}$ M histamine, a concentration which produces 90 to 100% of the tissue's maximum response to this agonist, had no protective effect when present during photoactivation (data not shown; n=4). This finding, and the 30-fold excess of AAH over DPH, argues against scavenging (Cooperman, 1976, vide supra) as a mechanism of the protection produced by DPH.

Figure 5:
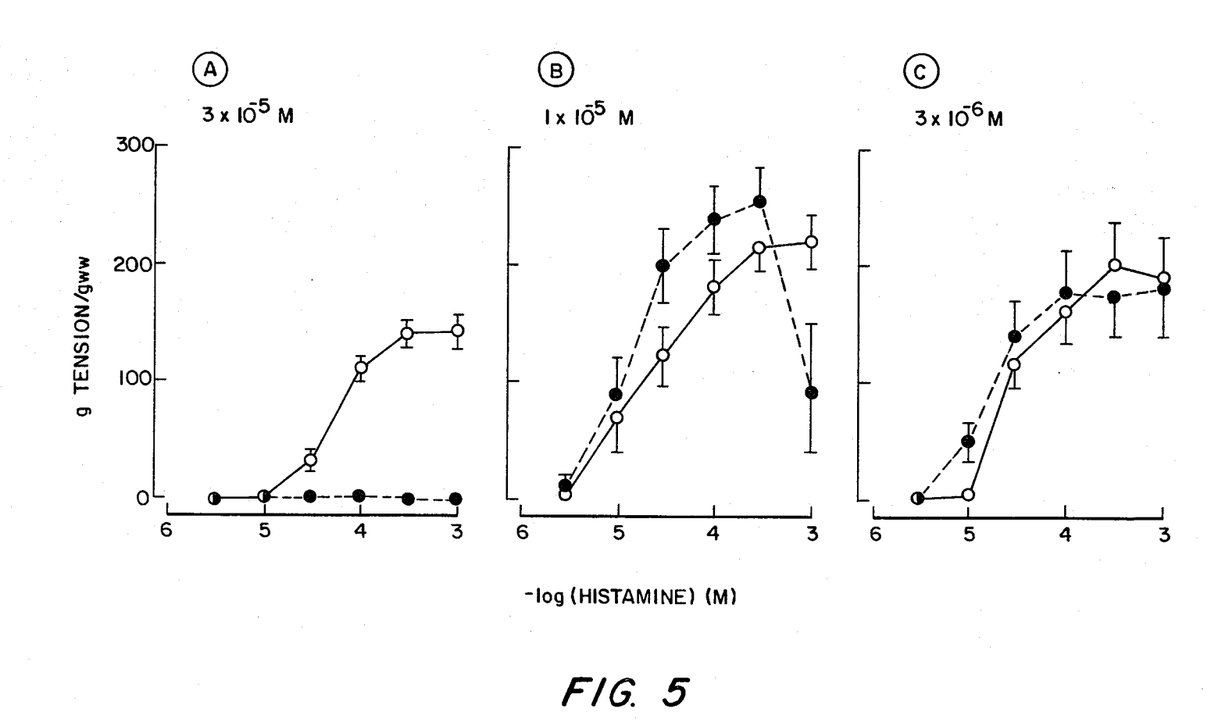
FIG. 5 shows histamine concentration-response curves obtained in the continual presence of nonirradiated AAH. (A) $3\times10^{-5}$ M AAH, n=4, (B) $10^{-5}$ M AAH, n=4, (C) $3\times10^{-6}$ M AAH, n=4. Open circles: non-irradiated controls; closed circles: AAH-exposed, continually present.

Effects of non-photoirradiated AAH. While non-photoirradiated AAH had no residual effect on responses to histamine after its washout (FIG. 2D), it was important to determine whether non-irradiated AAH behaved as a histamine antagonist when left present in the bath; i.e., that AAH had affinity for the histamine receptor. FIG. 5A shows that nonirradiated, $3 \times 10^{-5}$ M AAH abolished the response to histamine in a manner identical to that observed after its photolysis (see FIG. 2A). Somewhat similar to that seen after irradiation (FIG. 2B), a "bell-shaped" concentration-response curve resulted in the presence of $10^{-5}$ M AAH (FIG. 5B). Nonirradiated, $3 \times 10^{-6}$ M AAH caused a slight (2.01-fold) shift of the histamine concentration-response curve to the left of control (EC50's were 3.46 (3.16–3.77)$\times 10^{-5}$ M and 1.72 (1.67–2.01)$\times 10^{-5}$ M for control and AAH, respectively; $P<0.05$) (FIG. 5C). These results are in qualitative and quantitative agreement with these observed when AAH was photoirradiated and washed out (vide supra). Again, the antagonism was observed over a narrow (10-fold) range of concentration of AAH.

The specificity of the antagonism by nonirradiated AAH was examined. Non-irradiated, $3 \times 10^{-5}$ M AAH had no significant effect on concentration-response relationships for KCl (control: 25.0(20.7–30.3) mM; AAH: 15.3(11.1–21.2) mM; FIG. 6A) and ACh (control: 8.38 (5.31–13.23)$\times 10^{-6}$ M; AAH: 2.34 (0.91–6.03)$\times 10^{-6}$ M; FIG. 6D) but caused significant shifts of MgATP (12.89-fold; FIG. 6B) and norepinephrine (5.50-fold; FIG. 6C) concentration-response curves to the left of control. EC50 values obtained were as follows: for MgATP, control: $1.96(1.26-3.04)\times10^{-4}$ M and AAH: $1.52(1.31-1.76)\times10^{-5}$ M ($P<0.05$); for norepinephrine, control: $3.83(2.90-5.05)\times10^{-5}$ M and AAH; $6.96(3.61-13.43)\times10^{-6}$ M ($P<0.05$).

The results of the above indicate that photoactivated AAH is a very specific and irreversible histamine receptor antagonist in the isolated guinea-pig vas deferens. Evidence was obtained which suggests that activation of the compound with visible light results in the formation of an aryl nitrene intermediate which binds covalently to the receptor. It is believed that this compound is the first reported nonequilibrium competitive antagonist with specificity for the histamine receptor.

The chemical criteria which apply to the use of photoaffinity labels in biochemical studies are as follows. (1) The binding/receptor site should not be destroyed by the irradiation procedures. In this and a previous study (Hogaboom et al, 1980, supra) irradiation alone with high intensity visible light did not alter receptor function: responses to a wide variety of agonists, including histamine, were unaffected. Also, irradiation of tissues with ultraviolet light, which must be done using quartz vessels, decreased contractility of the vas deferens. (2) The label should bind reversibly in a non-covalent complex to the binding/receptor site prior to the formation of covalent complex. Moreover, the onset of permanent binding should be photoirradiation-dependent. FIG. 2D illustrates the incubation of the tissues in $3\times10^{-5}$ M AAH, without an irradiation step, followed by washout of the agent, had no residual affect on the histamine concentration-response curve. In contrast, irradiation of AAH during the latter 5 minutes of incubation with $3\times10^{-5}$ M resulted, after washout, in a complete and irreversible antagonism (FIG. 2A). Thus, unless the compound was photolyzed it had no irreversible effect on the tissues; this data confirms that the agent was not activated by some metabolic process in the tissue.

In the claims which follow, lower alkyl is $C_1-C_6$ carbons and may be either branched or straight chain.

We claim:

1. A method of producing irreversible $H_1$-histamine antagonism in vitro comprising irradiating an effective concentration of an antagonist selected from the group consisting of wherein $R_1$ is $NO_2$ and $R_2$ is H and $R_1$ is ortho to the amine group, and wherein $R_3$, $R_4$, $R_5$ and $R_6$ are H or lower alkyl groups with not more than two of the four positions substituted with a lower alkyl group with visible light in the presence of histamine receptor ligands.

2. The method of claim 1 wherein in the irreversible $H_1$-histamine antagonist $R_1$ is $NO_2$ and $R_2$ is H and $R_1$ is ortho to the amine group.

3. The method of claim 1 wherein in the irreversible $H_1$-histamine antagonist $R_3$, $R_4$, $R_5$ and $R_6$ are H or lower alkyl groups with not more than two of the four positions substituted with a lower alkyl group.

4. The method of claim 1 wherein in the irreversible $H_1$-histamine antagonist $R_4$ and $R_5$ are lower alkyl.

5. The method of claim 1 wherein the irreversible $H_1$-histamine antagonist is

4(5)-[2-(4-azido-2-nitroanilino)ethyl]imidazole hydrochloride.

6. The method of claim 1 wherein the effective concentration of the antagonist is from $3\times10^{-5}$ to $3\times10^{-6}$ M.

* * * * *